United States Patent [19]
Melzig et al.

[11] Patent Number: 5,707,557
[45] Date of Patent: Jan. 13, 1998

[54] PHOTOCHROMIC 3H-NAPHTHOPYRANS

[75] Inventors: Manfred Melzig, Wessling; Herbert Zinner, Taufkirchen, both of Germany

[73] Assignee: Optische Werke G. Rodenstock, Munich, Germany

[21] Appl. No.: 771,196

[22] Filed: Dec. 20, 1996

[30] Foreign Application Priority Data

Dec. 20, 1995 [DE] Germany .......... 195 47 570.4

[51] Int. Cl.$^6$ .......... G02B 5/23; C07D 311/92
[52] U.S. Cl. .......... 252/586; 549/389; 549/43; 549/58; 546/196; 548/454; 548/464; 548/525
[58] Field of Search .......... 252/586; 549/389, 549/43, 58; 546/196; 548/454, 464, 525

[56] References Cited

U.S. PATENT DOCUMENTS

| | | |
|---|---|---|
| 3,567,605 | 3/1971 | Becker . |
| 4,931,221 | 6/1990 | Heller . |
| 4,980,089 | 12/1990 | Heller . |
| 5,066,818 | 11/1991 | Gemert et al. . |
| 5,238,981 | 8/1993 | Knowles . |
| 5,274,132 | 12/1993 | Van Gemert . |
| 5,340,857 | 8/1994 | Van Gemert . |
| 5,369,158 | 11/1994 | Knowles . |
| 5,395,567 | 3/1995 | Van Gemert et al. . |
| 5,552,090 | 9/1996 | Van Gemert et al. .......... 252/586 |
| 5,552,091 | 9/1996 | Kumar .......... 252/586 |

FOREIGN PATENT DOCUMENTS

| | | |
|---|---|---|
| 625518 | 11/1994 | European Pat. Off. . |
| 629620 | 12/1994 | European Pat. Off. . |
| WO 94/00867 | 1/1994 | WIPO . |

*Primary Examiner*—Philip Tucker
*Attorney, Agent, or Firm*—Evenson, McKeown, Edwards & Lenahan P.L.L.C.

[57] ABSTRACT

Photochromic compounds with a 3H-naphthopyran structure having at least one pyrene moiety in the 3-position, a method for preparing such compounds, and the use of such compounds for producing photochromic articles from an organic synthetic material.

11 Claims, No Drawings

PHOTOCHROMIC 3H-NAPHTHOPYRANS

BACKGROUND OF THE INVENTION

The invention relates to photochromic 3H-naphthopyrans. Pyrans are a long-known class of photochromic compounds. They have the property of reversibly changing their color under the influence of light having a certain content of activating radiation, as for example sunlight or the light of a mercury vapor lamp. The activation, which is accompanied by coloration of the compound, is based on the opening of a bond in the pyran ring which is induced by the actinic light. The change back to the original, closed state occurs after removal of the ultraviolet light source, when the non-activated, colorless or faintly colored form occurs.

The photochromic 3H-naphthopyrans on which the invention is based have one of the following basic structures:

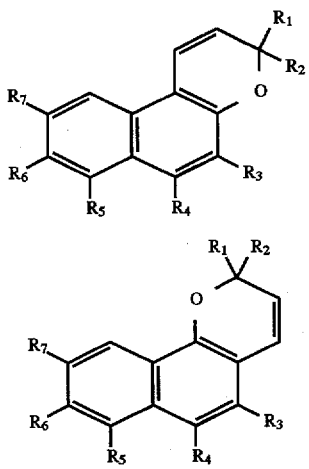

The basic chemical structure of the benzopyrans and naphthopyrans has already been described in U.S. Pat. No. 3,567,605. These compounds, which were patented in 1971, have a coloration dependent on irradiation with ultraviolet light only at temperatures in the −40° C. temperature range. They are therefore unsuited for use in common processes, such as the manufacture of eyeglasses, car sun roofs etc. Instead, for this purpose compounds are needed which color photochromically at normal temperatures, i.e., between +10° and +40° C.

A further development in the field of the naphthopyrans is the targeted introduction of selected substituents in the naphthalene part of the naphthopyran basic structure in order to obtain compounds which also color photochromically at normal temperatures. Such compounds are described, for example, in U.S. Pat. Nos. 5,238,981 and 5,369,158 and in published PCT Application No. WO 95/00867.

On the other hand it is known from various printed disclosures to improve the photochromic properties of the naphthopyrans by replacing the substituted or unsubstituted phenyl, naphthyl or heterocyclic aromatic moieties or the adamantane moiety in the 3H position of the naphthopyran structure, with specially selected, advantageous moieties. For example, U.S. Pat. No. 4,931,221 describes two cyclopropyl moieties in the 3H position in the naphthopyran basic structure. U.S. Pat. No. 4,980,089 describes benzo- and naphthospiropyrans which include a norcamphor- or tricyclodecane moiety. U.S. Pat. No. 5,274,132 describes photochromic naphthopyrans which have a substituent in the 3H position, which is bonded through an ethylene group to the pyran ring.

Also described as substituents in the 3H position on the naphthopyran structure in published European Patent Application No. EP 625,518 is an aromatic 5-ring moiety which can be configured as a fluorene structure by anellation of two benzene nuclei, and in U.S. Pat. No. 5,395,567 is a fluorene moiety or other polynuclear moiety. 3H naphthopyrans which have different, specially configured aryl and heteroaryl moieties in the 3H position are likewise disclosed in published European Patent Application No. EP 629,620.

In these known compounds there is the problem that an increase of the absorption cross section in the activated, darkened form, and thus an improvement in photochromic coloration, can be achieved only with a simultaneous bathochromic shift of the absorption maximum. This shift of the absorption maximum to the longer wavelength range is equivalent to an alteration of the color impression and is not desired.

To prevent this bathochromic shift, compounds are proposed in the prior art with aryl and heteroaryl substituents in the 3H position having auxochromic groups, such as —OCH$_3$. For example, in U.S. Pat. No. 5,066,818 naphthopyrans are described which are diaryl-substituted in the 3H position, at least one of the aryl substituents having an auxochromic group which causes a deepening of color in the colored state.

The introduction of the auxochromic groups lessens the bathochromic shift of the absorption maximum, while maintaining the high absorption cross section. These compounds, however, have the disadvantage that the life of the photochromic molecules is impaired by the auxochromic groups, so that the life of the products containing these compounds is limited.

Furthermore, it is known that the preparation of photochromic 3H naphthopyrans with an aryl substituent in position 3, which has more than two benzene or heteroaromatic nuclei, leads to very poor yields. Due to the low yields, 3-anthryl-3H-naphthopyrans, for example, cannot be prepared under economically practical conditions.

SUMMARY OF THE INVENTION

It is the object of the present invention to provide photochromic naphthopyrans which will have the advantageous properties known in the state of the art, such as a good photochromic effect at room temperature, a high darkening speed, and a suitable brightening speed, as well as a method for synthesizing them.

It is also an object of the invention to provide compounds which exhibit a low bathochromic shift of the absorption maximum in turning color and a great increase of the absorption cross section.

It is another object of the invention to provide photochromic compounds which exhibit a useful service life as long as that of the previously known compounds.

These and other objects are achieved in accordance with the present invention by providing a photochromic compound with a 3H-naphthopyran structure having at least one pyrene moiety in position 3, and corresponding to one of the following structures:

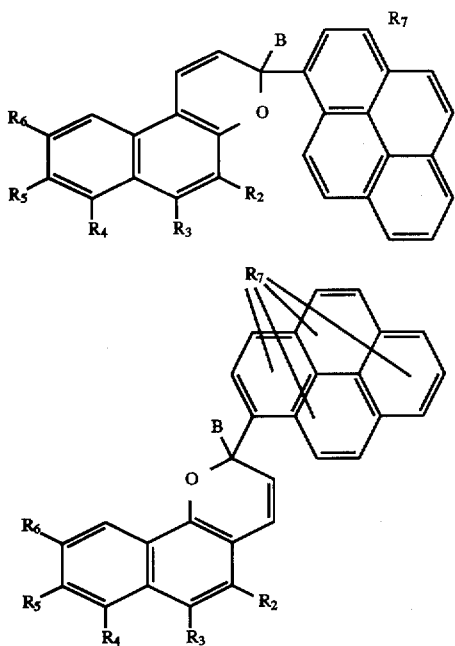

wherein

B represents alkyl, alkenyl, vinyl, a carbo- or heterocyclic ring system, in which one or more hydrogen atoms can be replaced with X independently of one another; X representing hydroxy, $C_1$–$C_6$-alkyl, $C_1$–$C_6$-alkoxy, phenoxy, $C_4$–$C_7$-cycloalkyl, halogen or NRR' wherein R and R' independently of one another represent hydrogen or $C_1$–$C_6$-alkyl, or together form a $C_4$–$C_7$-cycloalkyl moiety or a 5–7-member heterocyclic ring;

$R_2$ and $R_4$ through $R_7$ independently represent hydrogen, $C_1$–$C_6$-alkyl, $C_1$–$C_6$-alkoxy, $C_4$–$C_7$-cycloalkyl, halogen or NR"R'" wherein R" and R'" independently of one another represent hydrogen or $C_1$–$C_6$-alkyl, or together form a $C_4$–$C_7$-cycloalkyl moiety or a 5–7-member heterocyclic ring, $C_1$–$C_6$-carboxy($C_1$–$C_6$) alkyl, —O—($C_1$–$C_6$)carboxy-($C_1$–$C_6$)alkyl, cyano, $C_1$–$C_6$-acyl, $C_1$–$C_6$-acyloxy, substituted or unsubstituted arylacyloxy, substituted or unsubstituted aryloxy, substituted or unsubstituted aryl, or a 5–6-member substituted or unsubstituted heterocycle, wherein the substituent or substituents of the arylacyloxy, aryloxy or aryl moiety or of the 5–6-member heterocycle are independently selected from $C_1$–$C_6$-alkyl, $C_1$–$C_6$-alkoxy, $C_4$–$C_7$-cycloalkyl, halogen and cyano; and $R_3$ represents hydrogen, $C_1$–$C_6$-alkyl, $C_5$–$C_7$-cycloalkyl, $C_1$–$C_6$-carboxy($C_1$–$C_6$)alkyl, —O—($C_1$–$C_6$)carboxy-($C_1$–$C_6$)alkyl, $C_1$–$C_6$-acyl, $C_1$–$C_6$-acyloxy, cyano, or halogen.

In accordance with a further aspect of the invention, the objects have been achieved by providing a method of preparing a photochromic compound comprising the steps of:

1) a) reacting a pyrene with an acid chloride corresponding to the formula

to form a ketone, wherein

B represents alkyl, alkenyl, vinyl, a carbocyclic or heterocyclic ring system wherein one or more hydrogen atoms can be replaced by X independently of one another, X representing hydroxy, $C_1$–$C_6$-alkyl, $C_1$–$C_6$-alkoxy, phenoxy, $C_4$–$C_7$-cycloalkyl, halogen or NRR' wherein R and R' independently represent H or $C_1$–$C_6$-alkyl, or together form a $C_4$–$C_7$-cycloalkyl group or a 5–7-member heterocyclic ring;

or b) reacting a pyrenecarboxylic acid to form a pyrenecarboxylic acid chloride, and reacting the pyrenecarboxylic acid chloride with a moiety B, which has at least one aromatic ring, to form a ketone;

or c) reacting a pyrenecarboxylic acid to form a pyrenecarboxylic acid chloride and reacting the pyrenecarboxylic acid chloride with a moiety B, which has at least one p-hydroxyl aromatic group, to form a p-hydroxyketone;

2) reacting the ketone obtained in step 1) a), b) or c) with a metal acetylide to form an alkinol, and 3) reacting the alkinol obtained in step 2) with a 1-naphthol or a 2-naphthol.

DETAILED DESCRIPTION OF PREFERRED EMBODIMENTS

According to the invention it has been recognized that photochromic compounds are suitable to achieve the purposes of the invention which have a 3H naphthopyran structure carrying in position 3 at least one pyrene moiety and which exhibit one of the following structures I or II:

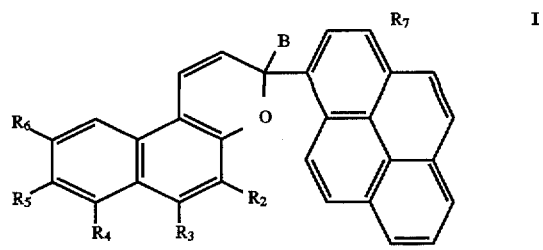

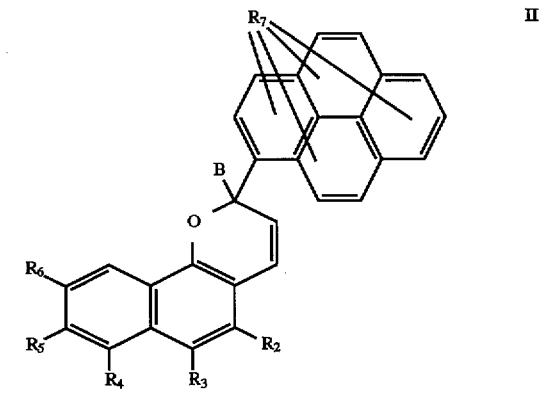

In these structural formulas the moieties $R_2$, and $R_4$ through $R_7$ represent, independently of one another: hydrogen, $C_1$–$C_6$-alkyl, $C_1$–$C_6$-alkoxy, $C_4$–$C_7$-cycloalkyl, halogen, NR"R'" wherein R" and R'" independently represent hydrogen or $C_1$–$C_4$-alkyl, or together form a $C_6$–$C_7$-cycloalkyl moiety or a 5–7-member heterocyclic ring (such as, for example, pyridine, piperidine, piperazine, pyrrole, pyrrolidine, pyrazole, pyrazoline, azepine, diazepine, oxazole, thiazole, or morpholine), $C_1$–$C_6$-carboxy($C_1$–$C_6$) alkyl (such as, for example, formic acid alkyl ester, acetic acid alkyl ester or propionic acid alkyl ester), —O— ($C_1$–$C_6$)-carboxy($C_1$–$C_6$)alkyl, cyano, $C_1$–$C_6$-acyl (such as, for example, acetyl or propionyl), $C_1$–$C_6$-acyloxy (such as, for example, acetoxy), substituted or unsubstituted arylacyloxy (such as, for example, benzoyloxy or naphthoyloxy), substituted or unsubstituted aryloxy (such as, for example, phenoxy or naphthoxy), substituted or unsubstituted aryl (such as, for example, phenyl or naphthyl), a five- or six-member substituted or unsubstituted heterocycle (such as, for example, pyridine, piperidine, methylpiperidine, pyrrole, furan, thiophene, oxazole, oxadiazole or methyloxadiazole), in which the substituent or substituents of arylacyloxy-, aryloxy- or aryl moiety, or of the five- or six-member heterocycle are independently selected from $C_1$–$C_6$-alkyl, $C_1$–$C_6$-alkoxy, $C_4$–$C_7$-cycloalkyl, halogen or cyano.

Preferably, the $R_2$ and $R_4$ through $R_7$ groups independently represent hydrogen, $C_1$–$C_3$-alkyl, $C_1$–$C_3$-alkoxy, $C_4$–$C_7$-cycloalkyl, fluorine, chlorine, bromine, iodine, NR"R'" (wherein R" and R'" independently represent hydrogen or $C_4$–$C_6$-alkyl, or together form a $C_4$–$C_7$-cycloalkyl moiety or a 5–6-member heterocyclic ring selected from the group, pyridine, piperidine, pyrrole and pyrrolidine), $C_1$–$C_3$-carboxy-($C_1$–$C_3$)alkyl (such as a formic acid alkyl ester, acetic acid alkyl ester or propionic acid alkyl ester), —O—($C_1$–$C_3$)-carboxy($C_1$–$C_3$)alkyl, cyano, $C_2$–$C_3$ acyl (such as acetyl or propionyl), acetoxy, mono- or di-substituted or unsubstituted benzoyloxy or naphthoyloxy, mono- or disubstituted or unsubstituted phenoxy or naphthoxy, mono- or disubstituted or unsubstituted phenyl or naphthyl, a five- or six-member substituted or unsubstituted heterocycle selected from the group pyridine, piperidine, pyrrole, furan, thiophene, oxazole, oxadiazole, wherein the substituent or substituents of the benzoyloxy-, naphthoyloxy-, phenoxy-, naphthoxy-, phenyl- or naphthyl moieties or of the five- or six-member heterocycle are independently selected from $C_1$–$C_3$-alkyl, $C_1$–$C_3$-alkoxy, $C_4$–$C_7$-cycloalkyl, fluorine, chlorine, bromine, iodine and cyano.

It is especially advantageous if the $R_2$ and $R_4$ through $R_7$ groups independently represent hydrogen, $C_1$–$C_3$-alkyl, $C_1$–$C_3$-alkoxy, $C_5$–$C_7$-cycloalkyl, fluorine, chlorine, bromine, iodine, NR"R'" (wherein R" and R'" independently represent $C_4$–$C_6$ alkyl, or together form a $C_4$–$C_7$ cycloalkyl moiety or a 5–6-member heterocyclic ring selected from the group pyridine, piperidine, pyrrole and pyrrolidine), $C_2$-carboxy($C_1$–$C_2$)alkyl (such as methyl acetate or ethyl acetate), cyano, acetyl, acetoxy, mono- or disubstituted or unsubstituted benzoyloxy, mono- or disubstituted or unsubstituted phenoxy, mono- or disubstituted or unsubstituted phenyl, a five- or six-member substituted or unsubstituted heterocycle selected from the group pyridine, piperidine, pyrrole, furan, thiophene, oxazole and oxadiazole, wherein the substituent or substituents of the benzoyloxy-, phenoxy- or phenyl moieties, or of the five- or six-member heterocycle are independently selected from $C_1$–$C_3$-alkyl, $C_1$–$C_3$-alkoxy, $C_5$–$C_7$-cycloalkyl, fluorine, chlorine, bromine, iodine and cyano.

In particular, the $R_2$ and $R_4$ through $R_7$ groups can be ethyl, methoxy, ethoxy, acetoxy, halogen (bromine) or 5-methyl-2-oxadiazoyl.

It is particularly preferred that the $R_7$ group be present up to three times on the pyrene structure and be selected from the group hydrogen, methyl, ethyl, halogen (fluorine, chlorine, bromine), cyano and methoxy.

Furthermore, it is also contemplated that the pyrene structure be only singly substituted by $R_7$, especially by bromine or methoxy. It is also especially advantageous if the $R_7$ moiety represents hydrogen, i.e., if the pyrene moiety is unsubstituted.

The $R_3$ moiety of the general formulas I and II is selected from the group:
hydrogen,
$C_1$–$C_6$-alkyl (such as, for example, methyl or ethyl),
$C_5$–$C_7$-cycloalkyl (such as, for example, cyclohexyl or cyclopentyl),
$C_1$–$C_6$-carboxy ($C_1$–$C_6$)alkyl,
—O—($C_1$–$C_6$)-carboxy($C_1$–$C_6$)alkyl,
$C_1$–$C_6$-acyl (such as, for example, acetyl),
$C_1$–$C_6$-acyloxy (such as, for example, acetoxy),
cyano, and
halogen.

Preferably the $R_3$ moiety is selected from the group hydrogen, $C_1$–$C_3$-alkyl (such as methyl, ethyl or propyl), $C_5$–$C_7$-cycloalkyl (such as, for example, cyclohexyl, cyclopentyl), $C_1$–$C_3$-acyloxy (such as, for example, methoxy, ethoxy or propoxy), cyano, fluorine, chlorine, bromine. It is especially advantageous when $R_3$ represents chlorine or ethyl.

The B moiety is selected from the group alkyl, alkenyl, vinyl, and carbocyclic or heterocyclic ring systems in which one or more hydrogen atoms can be replaced independently of one another by a group X.

Preferably the B moiety is selected from the group $C_1$–$C_6$-alkyl, $C_3$–$C_6$-alkenyl, vinyl, a carbocyclic ring system with one or two rings and 5 to 10 ring atoms, a heterocyclic ring system with one to three rings and 5 to 13 ring atoms and one or two hetero atoms selected from the group N, O and S. The carbocyclic or heterocyclic ring system can have one or more X substituents.

In particular, the B moiety can be selected from the group $C_1$–$C_6$-alkyl, $C_3$–$C_6$alkenyl, vinyl and the following groups which can be substituted one or more times by X: $C_5$–$C_6$-cycloalkyl, $C_5$–$C_6$-cycloalkenyl (e.g. cyclohexenyl), phenyl, naphthyl, furan, thiophene, benzofuran, 2,3-dihydrobenzofuran, 2,3-dihydrobenzothiophene, benzothiophene, dibenzofuran, dibenzothiophene, tetrahydroquinoline, piperidine, pyrrolidine, indole, indoline, coumarone, pyrrole and julolidine.

X represents a substituent selected from the group hydroxy, $C_1$–$C_6$-alkyl, $C_1$–$C_6$-alkoxy, phenoxy, $C_4$–$C_7$-cycloalkyl, halogen or NRR' wherein R and R' independently represent hydrogen or $C_1$–$C_6$-alkyl, or together form a $C_4$–$C_7$-cycloalkyl moiety or a 5–7-member heterocyclic ring (such as, for example, pyridine, piperidine, piperazine, pyrrole, pyrrolidine, pyrazole, pyrazoline, azepine, diazepine, oxazole, thiazole or morpholine).

Preferably, X represents a substituent selected from the group hydroxy, $C_1$–$C_3$-alkyl, $C_3$–$C_6$-alkoxy, phenoxy, $C_4$–$C_7$-cycloalkyl, fluorine, chlorine, bromine, amino, $C_1$–$C_3$-dialkylamino, pyridine, piperidine, pyrrole, thiazole and morpholine. If X represents a heterocyclic compound containing nitrogen, then the link to the carbocyclic or heterocyclic ring system takes place through this or one of these N atoms. In particular, X is selected from hydroxy, fluorine, chlorine and methyl.

Preferably, the number of $R_2$–$R_6$ groups on the 3H naphthopyrans according to the invention totals no more than three, especially one or two, insofar as the substituents do not represent hydrogen.

The claimed 3H-naphthopyran compounds may have $R_2$–$R_6$ groups in the naphthalene part, which each can have a number of different configurations. These substituents are already described in part in the prior art. The substituent B also can be selected from a large group. The decisive factor for the improved properties of the compounds of the invention is the introduction of the pyrene moiety in the 3H position. This replacement of the known (un) substituted phenyl and naphthyl moieties with a pyrene moiety leads, independently of the selection of the moieties $R_2$–$R_6$ and B, to improved properties, inasmuch as the absorption maximum of the pyrene moiety lies at a longer wavelength than that of moiety B. This is especially the case when the moiety B has no more than two anellated carbocyclic or heterocyclic rings.

The substitution according to the invention of the 3H naphthopyran structure with a pyrene moiety results in compounds which have photochromic properties comparable to the known compounds, namely high darkening speed and suitable brightening speed, and at the same time a great increase of the absorption cross section in the activated state, a low bathochromic shift of the absorption maximum, and improved service life.

The configuration of the substituents in position 3 on the naphthopyran structure according to the invention leads to an unexpected and surprising increase of the absorption cross section with greatly reduced bathochromic shift of the absorption maximum. It has furthermore been recognized that, as a result of the introduction of the pyran moiety, the substitution of the 3H substituents with auxochromic groups can be omitted.

A particular advantage resulting from the elimination of substituents in the pyrene part of the compounds of the invention is their increased service life in comparison to that of the known prior art compounds which exhibit a comparable absorption cross section and a similarly low bathochromic shift of the absorption maximum due to the introduction of auxochromic groups.

The method of preparing photochromic compounds according to the invention leads to good yields of the compounds of the invention. This is especially surprising to persons skilled in the art, since the synthesis of 3H naphthopyrans which have an anthracene substituent in the 3-position leads to very poor yields, and one skilled in the art would expect an even poorer outcome in the case of larger substituents, such as pyrene.

A method for preparing the photochromic compounds of the invention will next be described. The method is basically composed of three steps.

1. First a ketone is prepared with a pyrene moiety and the B moiety linked to its carbonyl group. For this purpose three possible methods of synthesis in accordance with the invention are claimed.

a) A pyrene or a substituted pyrene is reacted with an acid chloride. The acid chloride has the structure of the B moiety and contains the acid chloride group in the position through which the B moiety is later linked to the 3H-naphthopyran structure (e.g., pyrene, Aldrich, No. 18,551-5, Merck, No. 821051; 1-bromopyrene, Aldrich, No. 39,157-3; 1-methylpyrene from pyrene and chloromethane (Aldrich, No. 29,550-7, Merck No. 823243,) in $AlCl_3$; e.g., cyclohexenecarboxylic acid chloride, from cyclohexene-1-carboxylic acid methyl ester (Aldrich, No. 23,218-1) by reaction with $SOCl_2$, or from cyclohexanone (Merck, No. 822269) with NaCN, followed by hydrolysis and reaction with $SOCl_2$; benzofuran-2-carboxylic acid chloride from benzofuran-2-carboxylic acid (Aldrich, No. 30,727-0) by reaction with $SOCl_2$; thiophene-2-carboxylic acid chloride, Aldrich No. 28,898-5, Merck No. 814308; benzoyl chloride, Aldrich No. 24,054-0, Merck No. 801804; 2-fluorobenzoyl chloride, Aldrich No. 12,084-7; 3-fluorobenzoyl chloride, Aldrich No. 16,253-1, Merck No. 814262; N-methylpiperidine-3-carboxylic acid chloride, from N-methylpiperidine-3-carboxylic acid ethyl ester (Aldrich No. 19,435-2) by reaction with $SOCl_2$; N-methylindole-2-carboxylic acid chloride, from N-methylindole-2-carboxylic acid (Aldrich No. 13,415-5) by reaction with $SOCl_2$).

b) Pyrenecarboxylic acid or substituted pyrenecarboxylic acid is converted to the acid chloride with $SOCl_2$. The acid chloride is reacted with a 1.05-fold molar amount of moiety B. This method of synthesis is advantageous when the preparation of the acid chlorides which correspond to the moiety B is very complex or impossible. It is only possible, however, if the moiety B contains at least one aromatic ring, (e.g., pyrenecarboxylic acid, Aldrich No. 39,158-1; e.g., N-methyl-1,2,3,4-tetrahydroisoquinoline Merck No. 814200; coumarone, Aldrich No. B800-2; julolidine, Aldrich No. J100-1).

c) If moiety B contains an aromatic nucleus with a hydroxy group in the para position, then pyrenecarboxylic acid chloride is prepared as under b), and reacted with the hydroxy aromatic ring. The resulting ester rearranges upon heating with $AlCl_3$ to produce the para hydroxyketone (e.g., phenol, Merck No. 822296).

2. The ketone obtained in step 1 is treated under anhydrous conditions with a metal acetylide. An alkinol (such as 2-propyn-1-ol) is obtained which has the pyrene moiety and moiety B in the 1-position. (e.g., lithium acetylide-ethylenediamine complex, Aldrich No. 18,615-5).

3. The alkinol obtained in step 2 is reacted with a 1- or 2-naphthol derivative to produce the photochromic compound according to the invention. (e.g., 1-naphthol, Aldrich No. N199-2, Merck No. 822289; 2-naphthol, Aldrich No. 18,550-7, Merck No. 822290; 6-methoxy-2-naphthol, Fluka No. 65125; 6-bromo-2-naphthol, Aldrich No. B7,340-6; 7-methoxy-2-naphthol, Aldrich No. 36,750-8; 4-chloro-1-naphthol, Aldrich No. 31,740-3; 5-ethoxy-1-naphthol, from 1,5-dihydroxynaphthalene, Aldrich No. D11,560-6, by reaction with diethyl sulfate, Aldrich No. 32,028-5; 3-(5-methyl-2-oxadiazoyl)-2-naphthol from acetimidic acid ethyl ester hydrochloride, Aldrich No. 18,884-0, and 2-hydroxy-3-naphthoic acid hydrazide, Aldrich No. H4,660-0).

The invention will be described hereinafter with reference to the following non-limiting examples to which reference is expressly made regarding disclosure of all details of the invention not otherwise explained in the text.

EXAMPLE 1

1. Preparation of a Benzoyl Pyran
Method a:

A solution of 50.5 g (0.25 mole) of pyrene and 37.5 g (0.268 mole) of benzoyl chloride in 0.5 liters of benzene was treated, with stirring, at room temperature, with 50 g (0.375 mole) of powdered, anhydrous aluminum chloride, whereupon the temperature slightly increased. After one hour of stirring at room temperature, the mixture was extracted by shaking with water and then the benzene was thoroughly removed from the organic phase. The remaining oil was dissolved in dichloromethane and filtered through aluminum oxide.

Crude yield: 75.1 g of orange-colored oil=benzoyl pyrene (98% of the theoretical yield).

Method b:

A one-liter flask was provided with a magnetic stirrer, reflux condenser and connected by a hose to a bubble counter. Therein 110 g of pyrene-1-carboxylic acid in 400 ml of thionyl chloride was boiled with refluxing until the evolution of gas stopped. Then the excess thionyl chloride was distilled off. The orange-brown residue was recrystallized twice from benzene.

Yield: yellow needles=pyrene-1-carboxylic acid chloride 86% of the theoretical yield. Melting point: 139°–140° C.

66 g (0.25 mole) of the resulting pyrene-1-carboxylic acid chloride in 0.5 liter of benzene were reacted with stirring at room temperature with 50 g (0.375 mole) of powdered, anhydrous aluminum chloride. After stirring for one hour at room temperature, the mixture was extracted by shaking with water, and then the benzene was thoroughly removed from the organic phase. The residual oil was taken up in dichloromethane and filtered through a column of aluminum oxide.

Yield: 73 g of orange-colored oil=benzoyl pyrene (95% of the theoretical yield)

2. Preparation of a Benzoyl Pyrene Acetylide:

23.0 g (0.25 mole) of lithium acetylide-ethylene diamine complex were added at room temperature with stirring to a solution of 76.6 g (0.25 mole) of the benzoyl pyrene obtained in step 1 in 350 ml of anhydrous dimethyl sulfoxide, whereupon the temperature rose slightly. The mixture is stirred vigorously overnight, then ice was added, and after acidification with dilute hydrochloric acid it was thoroughly extracted with ether. After drying over sodium sulfate the solvent was removed.

Crude yield: 76.5 g of orange-colored oil=benzoyl pyrene acetylide (92% of the theoretical yield).

3. Preparation of Example 1 By Reaction With a 1-naphthol:

16.6 g (50 mmole) of the benzoyl pyrene acetylide obtained in step 2 was stirred for two hours at 65° C. in 100 ml of toluene together with 8.9 g (50 mmole) of 4-chloro-1-naphthol and a spatula-tip of toluene-4-sulfonic acid. After extracting by shaking with 5% caustic soda solution the mixture was dried over sodium sulfate, and the solvent was removed. The residual oil was dissolved in toluene and filtered through aluminum oxide. The collected fraction, which exhibited good red phototropic properties, crystallized out after two to three weeks.

Yield: 5.4 g of red crystals (22% of the theoretical yield).

EXAMPLE 2

The same procedure described in steps 1 and 2 of Example was followed.

16.6 g (50 mmole) of the benzoyl pyrene acetylide obtained in step 2 was stirred overnight at room temperature in 100 ml of toluene together with 7.9 g (50 mmole) of 6-methoxy-2-naphthol and a spatula tip of toluene-4-sulfonic acid. After extraction by shaking with 5% caustic soda solution, the mixture was dried over sodium sulfate and the solvent was removed. The residual oil was taken up in dichloromethane and filtered through aluminum oxide. One fraction was collected, which was strongly phototropic to orange; the solvent was extracted and then ether was added. After some time an orange powder precipitated.

Yield: 10.1 g of orange powder (41% of the theoretical yield).

COMPARATIVE EXAMPLE

The procedure of Example 1 was followed except 44.5 g (0.25 mole) of anthracene was used instead of pyrene. After steps 1 to 3 were performed, the yield was so poor that an insufficient amount of photochromic compound was available for comparative tests.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A photochromic compound with a 3H-naphthopyran structure having at least one pyrene moiety in position 3, and corresponding to one of the following structures:

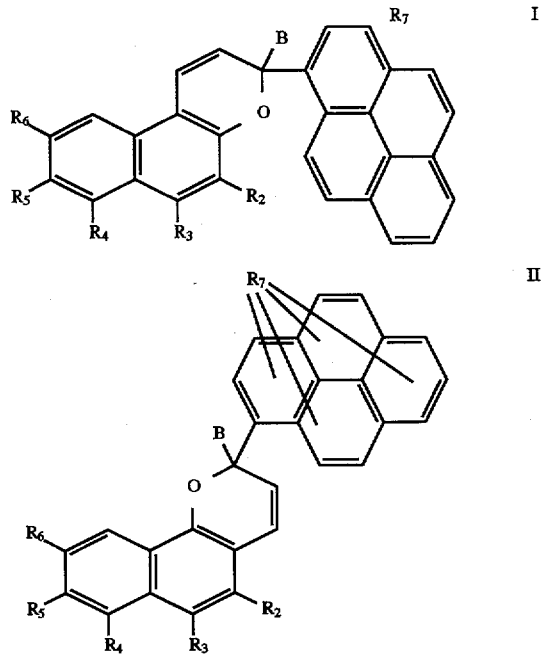

wherein:
B represents alkyl, alkenyl, vinyl, a carbo- or heterocyclic ring system with one to three rings and 5 to 13 ring atoms and one or two hetero atoms selected from the group N, O and S, in which one or more hydrogen atoms can be replaced with X independently of one another; X representing hydroxy, $C_1$–$C_6$-alkyl, $C_1$–$C_6$-alkoxy, phenoxy, $C_4$–$C_7$-cycloalkyl, halogen or NRR' wherein R and R' independently of one another represent hydrogen or $C_1$–$C_6$-alkyl, or together form a $C_4$–$C_7$-cycloalkyl moiety or a 5–7-member heterocyclic ring;

$R_2$ and $R_4$ through $R_7$ independently represent hydrogen, $C_1$–$C_6$-alkyl, $C_1$–$C_6$-alkoxy, $C_4$–$C_7$-cycloalkyl, halogen or NR"R'" wherein R" and R'" independently of one another represent hydrogen or $C_1$–$C_6$-alkyl, or together form a $C_4$–$C_7$-cycloalkyl moiety or a 5–7-member heterocyclic ring, $C_1$–$C_6$-carboxy($C_1$–$C_6$) alkyl, —O—($C_1$–$C_6$)carboxy-($C_1$–$C_6$)alkyl, cyano, $C_1$–$C_6$-acyl, $C_1$–$C_6$-acyloxy, substituted or unsubstituted arylacyloxy, substituted or unsubstituted aryloxy, substituted or unsubstituted aryl, or a 5–6-member substituted or unsubstituted heterocycle, wherein the substituent or substituents of the arylacyloxy, aryloxy or aryl moiety or of the 5–6-member heterocycle are independently selected from $C_1$–$C_6$-alkyl, $C_1$–$C_6$-alkoxy, $C_4$–$C_7$-cycloalkyl, halogen and cyano; and $R_3$ represents hydrogen, $C_1$–$C_6$-alkyl, $C_5$–$C_7$-cycloalkyl, $C_1$–$C_6$-carboxy($C_1$–$C_6$)alkyl, —O—($C_1$–$C_6$)carboxy-($C_1$–$C_6$)alkyl, $C_1$–$C_6$-acyl, $C_1$–$C_6$-acyloxy, cyano, or halogen.

2. A photochromic compound according to claim 1, wherein

B represents $C_1$–$C_6$-alkyl, $C_3$–$C_6$-alkenyl, vinyl, a carbocyclic ring system with one or two rings and 5 to 10 ring atoms, a heterocyclic ring system with one to three rings and 5 to 13 ring atoms and one or two hetero atoms selected from the group N, O and S, wherein in the carbo- or heterocyclic ring system one or more hydrogen atoms can be replaced with X independently of one another; X representing hydroxy, $C_1$–$C_3$-alkyl, $C_3$–$C_6$-alkoxy, phenoxy, $C_4$–$C_7$-cycloalkyl, fluorine, chlorine, bromine, NRR' wherein R and R' independently of one another represent hydrogen or $C_1$–$C_3$-alkyl, or together form a pyridine, piperidine, pyrrole, thiazole or morpholine ring;

$R_2$ and $R_4$ through $R_7$ independently of one another represent hydrogen, $C_1$–$C_3$-alkyl, $C_1$–$C_3$-alkoxy, $C_4$–$C_7$-cycloalkyl, fluorine, chlorine, bromine, iodine, NR"R'" wherein R" and R'" independently of one another represent hydrogen or $C_4$–$C_6$-alkyl, or together form a $C_4$–$C_7$-cycloalkyl moiety or a 5–6-member heterocyclic ring selected from the group pyridine, piperidine, pyrrole and pyrrolidine, $C_1$–$C_3$-carboxy ($C_1$–$C_3$)alkyl, —O—($C_1$–$C_3$)-carboxy($C_1$–$C_3$)alkyl, cyano, $C_2$–$C_3$-acyl, acetoxy, mono- or disubstituted or unsubstituted benzoyloxy or naphthoyloxy, mono- or disubstituted or unsubstituted phenoxy or naphthoxy, mono- or disubstituted or unsubstituted phenyl or naphthyl, a 5–6-member substituted or unsubstituted heterocycle selected from the group pyridine, piperidine, pyrrole, furan, thiophene, oxazole, oxadiazole, wherein the substituent or substituents of the benzoyloxy, naphthoyloxy, phenoxy, naphthoxy, phenyl or naphthyl moieties or of the 5–6-member heterocycle are independently selected from $C_1$–$C_3$-alkyl, $C_1$–$C_3$-alkoxy, $C_4$–$C_7$-cycloalkyl, fluorine, chlorine, bromine, iodine and cyano; and $R_3$ represents hydrogen, $C_1$–$C_3$-alkyl, $C_5$–$C_7$-cycloalkyl, $C_1$–$C_3$-acyloxy, cyano, fluorine, chlorine or bromine.

3. A photochromic compound according to claim 1, wherein

B represents $C_1$–$C_6$-alkyl, $C_3$–$C_6$-alkenyl, vinyl or any of the following groups which can be substituted one or more times by X: $C_5$–$C_6$-cycloalkyl, $C_5$–$C_6$-cycloalkenyl, phenyl, naphthyl, furan, thiophene, benzofuran, 2,3-dihydrobenzofuran, benzothiophene, 2,3-dihydrobenzothiophene, dibenzofuran, dibenzothiophene, tetrahydroquinoline, piperidine, pyrrolidine, indole, indoline, coumarone, pyrrole, julolidine; X representing hydroxy, fluorine, chlorine or methyl;

$R_2$ and $R_4$ through $R_7$ independently of one another represent hydrogen, $C_1$–$C_3$-alkyl, $C_1$–$C_3$-alkoxy, $C_5$–$C_7$-cycloalkyl, fluorine, chlorine, bromine, iodine, NR"R'" wherein R" and R'" independently represent $C_4$–$C_6$-alkyl or together form a $C_4$–$C_7$-cycloalkyl moiety or a 5–6-member heterocyclic ring selected from the group, pyridine, piperidine, pyrrole and pyrrolidine, $C_2$-carboxy ($C_1$–$C_2$)alkyl, cyano, acetyl, acetoxy, mono- or disubstituted or unsubstituted benzoyloxy, mono- or disubstituted or unsubstituted phenoxy, mono- or disubstituted or unsubstituted phenyl, a 5–6-member substituted or unsubstituted heterocycle selected from the group pyridine, piperidine, pyrrole, furan, thiophene, oxazole, oxadiazole, wherein the substituent or substituents of the benzoyloxy, phenoxy, phenyl or of the 5–6-member heterocycle are independently selected from $C_1$–$C_3$ alkyl, $C_1$–$C_3$ alkoxy, $C_5$–$C_7$ cycloalkyl, fluorine, chlorine, bromine, iodine and cyano; and $R_3$ represents chlorine or ethyl.

4. A photochromic compound according to claim 1, wherein $R_2$ and $R_4$ through $R_7$ are independently selected from ethyl, methoxy, ethoxy, acetoxy, bromine and 5-methyl-2-oxadiazoyl.

5. A photochromic compound according to claim 1, wherein $R_7$ is hydrogen, methyl, ethyl, fluorine, chlorine, bromine, cyano or methoxy, and wherein if $R_7$ is not hydrogen, the pyrene moiety is substituted no more than three times by $R_7$.

6. A photochromic compound according to claim 1, wherein $R_7$ represents hydrogen, bromine or methoxy, and wherein if $R_7$ is not hydrogen, the pyrene moiety is substituted only once by $R_7$.

7. A photochromic compound according to claim 1, wherein $R_7$ represents hydrogen.

8. A method of preparing a photochromic compound comprising the steps of:
1) a) reacting a pyrene with an acid chloride corresponding to the formula

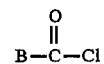

to form a ketone, wherein

B represents alkyl, alkenyl, vinyl, a carbocyclic or heterocyclic ring system with one to three rings and 5 to 13 ring atoms and one or two hetero atoms selected from the group N, O and S, wherein one or more hydrogen atoms can be replaced by X independently of one another, X representing hydroxy, $C_1$–$C_6$-alkyl, $C_1$–$C_6$-alkoxy, phenoxy, $C_4$–$C_7$-cycloalkyl, halogen or NRR' wherein R and R' independently represent H or $C_1$–$C_6$-alkyl, or together form a $C_4$–$C_7$-cycloalkyl group or a 5–7-member heterocyclic ring;

or b) reacting a pyrenecarboxylic acid to form a pyrenecarboxylic acid chloride, and reacting the pyrenecarboxylic acid chloride with a moiety B, which has at least one aromatic ring, to form a ketone;

or c) reacting a pyrenecarboxylic acid to form a pyrenecarboxylic acid chloride and reacting the pyrenecarboxylic acid chloride with a moiety B, which has at least one p-hydroxyl aromatic group, to form a p-hydroxyketone;

2) reacting the ketone obtained in step 1) a), b) or c) with a metal acetylide to form an alkinol, and 3) reacting the alkinol obtained in step 2) with a 1-naphthol or a 2-naphthol.

9. A method according to claim 8, wherein

B represents $C_1$–$C_6$-alkyl, $C_3$–$C_6$-alkenyl, vinyl, a carbocyclic ring system with one or two rings and 5 to 10 carbon atoms, a heterocyclic ring system with one to three rings and 5 to 13 ring atoms and one or two hetero atoms selected from the group N, O and S, wherein in the carbocyclic or heterocyclic ring system one or more hydrogen atoms can be replaced independently of one another by X, X representing hydroxy, $C_1$–$C_3$-alkyl, $C_3$–$C_6$-alkoxy, phenoxy, $C_4$–$C_7$-cycloalkyl, fluorine, chlorine, bromine, or NRR' wherein R and R' independently represent hydrogen or $C_1$–$C_3$-alkyl, or together form a pyridine, piperidine, pyrrole, thiazole or morpholine ring.

10. A method according to claim 8, wherein B represents $C_1$–$C_6$-alkyl, $C_3$–$C_6$-alkenyl, vinyl or any of the following groups which can be substituted one or more times by X: $C_5$–$C_6$ cycloalkyl, $C_5$–$C_6$-cycloalkenyl, phenyl, naphthyl, furan, thiophene, benzofuran, 2,3-dihydrobenzofuran, benzothiophene, 2,3-dihydrobenzothiophene, dibenzofuran, dibenzothiophene, tetrahydroquinoline, piperidine, pyrrolidine, indole, indoline, coumarone, pyrrole, julolidine, X representing hydroxy, fluorine, chlorine or methyl.

11. A photochromic article comprising an organic synthetic resin material containing a photochromic compound according to claim 1.

* * * * *